(12) United States Patent
Säll et al.

(10) Patent No.: US 11,724,040 B2
(45) Date of Patent: Aug. 15, 2023

(54) AUTOMATIC FEEDBACK MECHANISM AND A MEDICAMENT DELIVERY DEVICE WITH USER FEEDBACK CAPABILITY

(71) Applicant: SHL MEDICAL AG, Zug (CH)

(72) Inventors: Daniel Säll, Segeltorp (SE); Daniel Carlsson, Enskede (SE)

(73) Assignee: SHL MEDICAL AG, Zug (CH)

(*) Notice: Subject to any disclaimer, the term of this patent is extended or adjusted under 35 U.S.C. 154(b) by 61 days.

(21) Appl. No.: 17/391,865

(22) Filed: Aug. 2, 2021

(65) Prior Publication Data

US 2021/0361878 A1 Nov. 25, 2021

Related U.S. Application Data

(63) Continuation of application No. 16/076,264, filed as application No. PCT/EP2017/051039 on Jan. 19, 2017, now Pat. No. 11,116,910.

(30) Foreign Application Priority Data

Feb. 16, 2016 (EP) .................................. 16155880

(51) Int. Cl.
*A61M 5/315* (2006.01)
*A61M 5/20* (2006.01)
*A61M 5/31* (2006.01)

(52) U.S. Cl.
CPC ...... *A61M 5/31566* (2013.01); *A61M 5/2033* (2013.01); *A61M 2005/2013* (2013.01);
(Continued)

(58) Field of Classification Search
CPC ........ A61M 5/31566; A61M 2205/581; A61M 2205/582; A61M 5/2033;
(Continued)

(56) References Cited

U.S. PATENT DOCUMENTS

| 2013/0035642 A1* | 2/2013 | Daniel | A61M 5/2033 604/189 |
| 2016/0008542 A1 | 1/2016 | Hirschel et al. | |
| 2016/0250417 A1* | 9/2016 | Olson | A61M 5/31596 604/228 |

FOREIGN PATENT DOCUMENTS

| EP | 2823841 A1 | 1/2015 |
| EP | 3184134 A1 | 6/2017 |
| (Continued) | | |

OTHER PUBLICATIONS

International Search Report and Written Opinion for Int. App. No. PCT/EP2017/051039 dated Apr. 26, 2017.

*Primary Examiner* — James D Ponton
*Assistant Examiner* — Neeraja Gollamudi
(74) *Attorney, Agent, or Firm* — McDonnell Boehnen Hulbert & Berghoff LLP

(57) ABSTRACT

An automatic feedback mechanism for a medicament delivery device that notifies a user of a start of expulsion of medicament from a medicament container is presented where a plunger rod, a tubular extension member arranged to receive the plunger rod in the radial space, and wherein the tubular extension member has flexible tongues configured to releasably lock the plunger rod in a pre-tensioned state. The tubular operation member is arranged to receive the tubular extension member, where the tubular operation member in a first position is arranged to press the flexible tongues radially inwards to lock the plunger rod in the pre-tensioned state. A first resilient member is arranged inside the plunger rod to exert a force in the proximal direction. A signal generating member is arranged to partially surround the plunger rod such that movement of the signal generating member distally hits the inner distal surface generating an audible signal.

8 Claims, 8 Drawing Sheets

(52) U.S. Cl.
CPC .............. *A61M 2005/2073* (2013.01); *A61M 2005/3125* (2013.01); *A61M 2205/581* (2013.01); *A61M 2205/582* (2013.01)

(58) Field of Classification Search
CPC .. A61M 2005/3125; A61M 2005/2073; A61M 2005/2013; A61M 2205/58
See application file for complete search history.

(56) References Cited

FOREIGN PATENT DOCUMENTS

| | | |
|---|---|---|
| TW | I517871 B | 1/2016 |
| TW | I519331 B | 2/2016 |
| TW | I520757 B | 2/2016 |
| WO | 2011/099918 A1 | 8/2011 |
| WO | 2011/123024 A1 | 10/2011 |

* cited by examiner

AUTOMATIC FEEDBACK MECHANISM AND A MEDICAMENT DELIVERY DEVICE WITH USER FEEDBACK CAPABILITY

CROSS REFERENCE TO RELATED APPLICATIONS

The present application a continuation of U.S. patent application Ser. No. 16/076,264, filed Aug. 7, 2018, which is a U.S. National Phase Application pursuant to 35 U.S.C. § 371 of International Application No. PCT/EP2017/051039 filed Jan. 19, 2017, which claims priority to European Patent Application No. 16155880.4 filed Feb. 16, 2016. The entire disclosure contents of these applications are herewith incorporated by reference into the present application.

TECHNICAL FIELD

The present disclosure generally relates to medical devices. In particular, it relates to an automatic feedback mechanism for a medicament delivery device and to a medicament delivery device comprising such an automatic feedback mechanism, which thereby provides user feedback.

BACKGROUND

When handling a medicament delivery device, it may be beneficial to provide visual and/or tactile indication to a user regarding the current state of the medicament delivery device. For example, it is typically required that an automated medicament delivery device is maintained in position at the injection site until the expelled dose has been properly absorbed and the liquid pressure created by the injected dose has subsided in the injection site area. To this end, for automated medicament delivery devices it may be advantageous for a user to know when the dose expulsion commences, facilitating determination of when the medicament delivery device may be removed from the injection site.

US2016/0008542 discloses an auto-injector for dispensing a liquid product with the intention to generate an acoustic and/or tactile signal. The device includes a housing, a container, a blocking sleeve, a drive member, a spring, a needle protection sleeve, and a holding element supporting the spring. In the initial state, the holding element is engaged with the drive member, which holding element is further maintained in position by the inner circumference of the blocking sleeve. To administer the product from the container the needle protection sleeve is moved by an activation stroke. The holding element is thereby disengaged from the drive member, and is instead set into engagement with the blocking sleeve. The drive member is thereby released. The holding element can hence be moved some distance relative to the housing, whereby the holding element transports the blocking sleeve. This causes the blocking sleeve to strike against a start signal stop formed by a mechanical holder. An acoustic and/or tactile signal is thereby emitted and signals the user of the device that dispensing of the product has started.

The disclosure of US2016/0008542 provides a solution for a specific configuration or design of an auto-injector. Moreover, the acoustic and/or tactile signal is not really provided at the time when liquid expulsion commences.

SUMMARY

A general object of the present disclosure is to provide an automatic feedback mechanism for a medicament delivery device, and a medicament delivery device comprising such an automatic feedback mechanism, which solve or at least mitigate the problems of the prior art.

There is hence according to a first aspect of the present disclosure provided an automatic feedback mechanism for a medicament delivery device, which notifies a user of a start of expulsion of medicament from a medicament container, wherein the automatic feedback mechanism comprises: a plunger rod, a tubular extension member having a radial space defined by an inner perimeter and an inner distal surface, wherein the tubular extension member is arranged to receive the plunger rod in the radial space, and wherein the tubular extension member has flexible tongues configured to releasably lock the plunger rod in a pre-tensioned state, a tubular operation member arranged to receive the tubular extension member, which tubular operation member is movable relative to the tubular extension member, wherein the tubular operation member in a first position is arranged to press the flexible tongues radially inwards to lock the plunger rod in the pre-tensioned state, a first resilient member arranged to be received inside the plunger rod to exert a force in the proximal direction, and a signal generating member arranged to partially surround the plunger rod and having a distal transversal end portion which in a first position is at a distance D from the inner distal surface of the tubular extension member when the plunger rod is in the pre-tensioned state, wherein in an assembled state, movement of the tubular operation member causes the flexible tongues to expand radially releasing the plunger rod to travel proximally and allowing the first resilient member to move the signal generating member distally the distance D such that the distal transversal end portion hits the inner distal surface generating an audible signal.

A audible indication of medicament expulsion may thereby be provided to a user.

The tubular operation member may according to one variation be rotatable relative to the tubular extension member, wherein the tubular operation member in a first rotational position is arranged to press the flexible tongues radially inwards to lock the plunger rod in the pre-tensioned state. Thus, in an assembled state movement by rotation of the tubular operation member causes the flexible tongues to expand radially releasing the plunger rod.

According to one embodiment the signal generating member comprises an elongated U-shaped bracket having two longitudinally extending flexible legs provided with angled radial feet extending radially outward to secure the signal generating member in the first position.

According to one embodiment the radial feet in the first position have a radial extension that exceeds the transverse dimension of the radial space of the tubular extension member and where the radial feet in a second position have a radial extension that is less than the transverse dimension of the radial space of the tubular extension member.

According to one embodiment the radial feet in the first position have a radial extension that exceeds the radial extension of the radial feet when in the second position.

According to one embodiment the plunger rod has an external surface which has a first section provided with a first guide structure arranged to support and flex the signal generating member radially outwards, and to guide axial displacement of the signal generating member.

According to one embodiment in the initial position of the plunger rod the axial overlap between the first section and the signal generating member corresponds to the distance of axial displacement of the plunger rod necessary for commencement of medicament expulsion.

According to one embodiment the signal generating member has legs arranged to interact with the first guide structure.

According to one embodiment first guide structure comprises axial grooves in which the signal generating member is arranged to slide.

According to one embodiment the plunger rod has a second section arranged distally from and contiguous to the first section, which second section is defined by a longitudinal axially extending radial opening axially aligned with the first guide structure, allowing radial inwards flexing of the signal generating member towards its radially unbiased state.

According to one embodiment the second section extends to the distal end of the plunger rod.

According to one embodiment the plunger rod has a third section arranged distally from and contiguous to the second section, which third section is defined by a second guide structure axially aligned with the longitudinal axially extending radial opening, and arranged to support and flex the signal generating member radially outwards.

According to one embodiment the tubular extension member has first engagement means for engaging with the signal generating member in the initial position of the plunger rod, and wherein the tubular extension member has radial openings arranged distally from and aligned with the first engagement means, for allowing the signal generating member to flex radially outwards.

According to one embodiment the first section extends to the distal end of the plunger rod.

According to a second aspect of the present disclosure there is provided a medicament deliver device comprising a feedback mechanism according to the first aspect.

One embodiment comprises a linearly displaceable medicament delivery member cover configured to interact with the tubular operation member.

According to another aspect there is provided a medicament delivery device comprising a housing having a proximal end and a distal end, a plunger rod received by the housing and axially displaceable from an initial position to a final position relative to the housing, a tubular extension member received by the housing and arranged to receive the plunger rod, which tubular extension member has a distal inner surface, a U-bracket received by the tubular extension member, wherein the plunger rod is arranged to be received by the U-bracket, and a first energy accumulation member arranged to bias the plunger rod in a proximal direction towards the proximal end and to bias the U-bracket in a distal direction which is opposite to the proximal direction, wherein in the initial position the plunger rod is arranged to flex the U-bracket radially outward towards the tubular extension member thereby engaging the U-bracket with the tubular extension member, whereby the U-bracket is distanced from the distal inner surface of the tubular extension member, and wherein the plunger rod and the U-bracket are arranged to allow the U-bracket to flex radially inwards towards a radially unbiased state of the U-bracket to disengage from the tubular extension member upon an axial displacement of the plunger rod corresponding to a distance necessary for commencement of medicament expulsion, thereby providing axial displacement of the biased U-bracket to the distal inner surface of the tubular extension member.

Since the U-bracket is released from the tubular extension member when the plunger rod has been displaced a distance corresponding to the distance necessary for commencement of medicament expulsion, the biased U-bracket will rapidly be thrown in the distal direction and collide with the distal inner surface of the tubular extension member when medicament expulsion has just commenced. In other words, the audible and/or tactile feedback provided by this collision will occur essentially when medicament expulsion has just commenced. A user of the medicament delivery device will thereby be provided with a rather precise indication of the commencement of dose expulsion.

According to one embodiment the U-bracket has two radial arms, wherein the radial feet are arranged to engage with the tubular extension member in the initial position of the plunger rod.

According to one embodiment the plunger rod has a distal end opening, wherein the first energy accumulation member is arranged in and extends from the distal end opening.

According to one embodiment U-bracket has a distal transverse end portion, and wherein the distal end of the first energy accumulation member bears against the distal transverse end portion, thereby biasing the U-bracket in the distal direction.

According to one embodiment the plunger rod has an external surface which has a first section provided with a first guide structure arranged to support and flex the U-bracket radially outwards, and to guide axial displacement of the U-bracket.

According to one embodiment in the initial position of the plunger rod the axial overlap between the first section and the U-bracket corresponds to the distance of axial displacement of the plunger rod necessary for commencement of medicament expulsion.

According to one embodiment the U-bracket has legs arranged to interact with the first guide structure.

According to one embodiment the first guide structure comprises axial grooves in which the U-bracket is arranged to slide.

According to one embodiment the plunger rod has a second section arranged distally from and contiguous to the first section, which second section is defined by a longitudinal axially extending radial opening aligned with the first guide structure, allowing radial inwards flexing of the U-bracket towards its radially unbiased state.

According to one embodiment the second section extends to the distal end of the plunger rod.

According to one embodiment the tubular extension member has first engagement means for engaging with the U-bracket in the initial position of the plunger rod, and wherein the tubular extension member has radial openings arranged distally from the first engagement means, for allowing the U-bracket to flex radially outwards.

According to one embodiment the tubular extension member has first engagement means for engaging with the U-bracket in the initial position of the plunger rod, and wherein the tubular extension member has radial openings arranged distally from and aligned with the first engagement means, for engaging with the U-bracket following radial outwards flexing of the U-bracket by the third section of the plunger rod.

According to one embodiment the first section extends to the distal end of the plunger rod.

One embodiment comprises a tubular rotator and a linearly displaceable medicament delivery member cover, wherein the tubular rotator is rotatable, by linear displacement of the medicament delivery member cover, between a first rotational position in which the tubular rotator is arranged to prevent the plunger rod from axial displacement from its initial position, and a second rotational position, wherein the tubular rotator and the tubular extension member are arranged to interact such that rotation of the tubular rotator towards the second rotational position releases the plunger rod to allow axial displacement of the plunger rod.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

Figure 1:
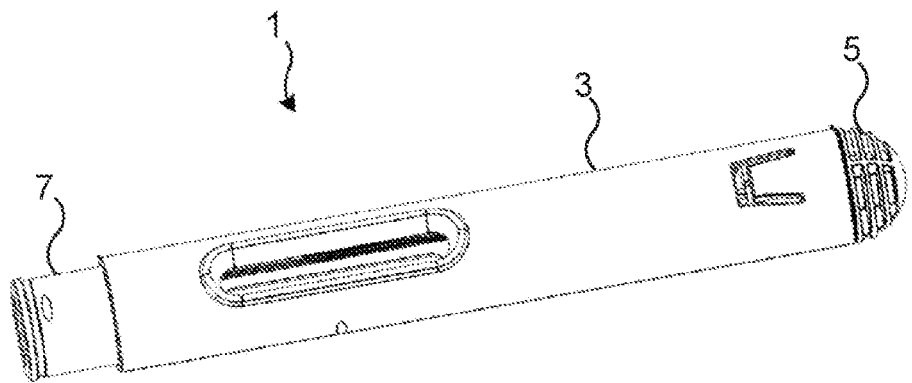
FIG. 1 shows a perspective view of an example of a medicament delivery device.

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The medicament delivery device disclosed herein may for example a disposable single-use medicament delivery device, such as an auto-injector, an inhaler or an eye dispenser. The medicament delivery device may be a regular medicament delivery device for medicament administration, or a trainer device.

The term "proximal end" as used herein refers to that end of a medicament delivery device at which medical expulsion can be provided. This is hence that end of the medicament delivery device that is to be pointed towards the injection or expulsion site. This definition also extends to any internal or external component of the medicament delivery device, i.e. the proximal end of any component is that which is closest to the proximal end of the medicament delivery device. The "distal end" is the opposite end relative to the proximal end. With "proximal direction" is meant a direction from the distal end towards the proximal end, along the central axis of the medicament delivery device. With "distal direction" is meant the opposite direction to "proximal direction".

This disclosure concerns an automatic feedback mechanism for a medicament delivery device, and to a medicament delivery device with user feedback capabilities.

The medicament delivery device has a housing having a proximal end and a distal end, a plunger rod received by the housing and axially displaceable from an initial position to a final position relative to the housing, a tubular extension member received by the housing and arranged to receive the plunger rod, which tubular extension member has a distal inner surface, a signal generating member received by the tubular extension member, wherein the plunger rod is arranged to be received by the signal generating member, and a first energy accumulation member arranged to bias the plunger rod in a proximal direction towards the proximal end and to bias the signal generating member in a distal direction which is opposite to the proximal direction.

In the initial position the plunger rod, which in the initial position is in a pre-tensioned state, is arranged to flex or press the signal generating member radially outward towards the tubular extension member thereby engaging the signal generating member with the tubular extension member. To this end, the plunger rod has a first section with a first thickness or dimension, which presses the signal generating member which in the initial position is mounted around the plunger rod, radially outwards. The signal generating member is thereby engaged with the tubular extension member, retaining the distally biased signal generating member in a fixed axial position relative to the housing. In this axial position, the signal generating member is distanced from the distal inner surface of the tubular extension member.

Prior to use, the plunger rod is arranged axially fixed in the initial position. When the medicament delivery device is activated, i.e. when a user initiates medicament delivery, the plunger rod is released from the initial position and is pressed in the proximal direction by the energy accumulation member. When the plunger rod has been displaced a distance corresponding to a distance necessary for commencement of medicament expulsion, the contact between the first section of the plunger rod and the signal generating member will cease. The plunger rod and the signal generating member are thus designed such that the axial overlap of the first section and signal generating member in the initial position of the plunger rod corresponds to, i.e. is equal to or essentially equal to, said distance. Hence, the first section only supports the signal generating member during axial displacement of the plunger rod distance corresponding to a distance necessary for commencement of medicament expulsion. When the plunger rod has been displaced by an amount corresponding to this distance, the signal generating member will be allowed to flex radially inwards towards its radially unbiased state. The signal generating member will thereby disengage from the tubular extension member. The signal generating member, which is biased in the distal direction by the first energy accumulation member will thereby no longer be retained by the tubular extension member and will therefore be thrown towards the distal inner surface of the tubular extension member. This results in an audible "click" sound, and also provides the user with a tactile sensation.

The medicament delivery device may furthermore comprise a medicament delivery member cover received by and rotationally interlocked with the housing, and a tubular rotator arranged to receive the plunger rod and the tubular extension member. The medicament delivery member cover is displaceable axially, between an extended position and a retracted position relative to the housing. The medicament delivery member cover is biased towards the extended position.

The tubular rotator is arranged to interact with the medicament delivery member, and has a guide structure arranged to convert linear motion of the medicament delivery member to rotational motion of the tubular rotator.

FIG. 1 shows an example of a medicament delivery device. The medicament delivery device 1 comprises a housing 3, having a proximal end 3a and a distal end 3b, a tubular extension member 5, for example a rear cap member, mounted at the distal end of the housing 3, and a medicament delivery member cover 7, e.g. a needle cover, arranged to be received by the housing 3 and arranged to be biased in the proximal direction.

Figure 2:
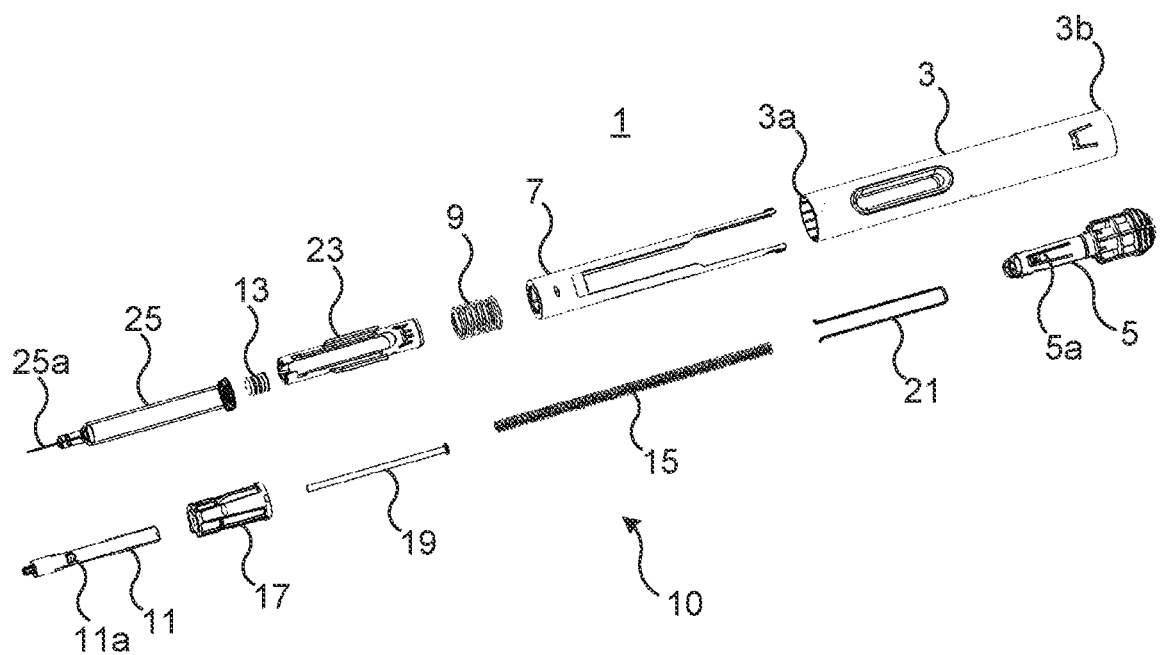
FIG. 2 is an exploded view of the medicament delivery device in FIG. 1.

FIG. 2 depicts an exploded view of the medicament delivery device 1. The medicament delivery device 1 further comprises a plunger rod 11 which is arranged to be biased towards the proximal end 3a, a plunger 13, a first resilient member, i.e. an energy accumulation member, 15 arranged to bias the plunger rod 11 in the proximal direction, which first energy accumulation member 15 may be a spring for example, a second resilient member or energy accumulation member 9, arranged to bias the medicament delivery member cover 7 in the proximal direction, a tubular rotator 17 arranged to receive the plunger rod 11 and the first energy accumulation member 15, tubular extension member 5 which is axially and rotationally fixed relative to the housing 3, a tubular operation member 17, in the following referred to as tubular rotator 17, arranged to receive a portion of the rear end cap 7 and the plunger rod 11, a rod 19 which the first energy accumulation member 15 is arranged to receive, and a signal generating member 21, which in the following will be exemplified by a U-shaped bracket, hereinafter referred to as "U-bracket". The exemplified medicament delivery device 1 furthermore comprises a medicament container holder 23 and a medicament container 25 provided with a needle 25a. The plunger 13 is arranged to run in the medicament container 25 by linear displacement of the plunger rod 11, to thereby expel medicament through the needle 25a.

The plunger rod 11, the tubular extension member 5, the tubular operation member 17, the energy accumulation member 15 and the signal generating member 21 form an automatic feedback mechanism 12, or simply a feedback mechanism, for the medicament delivery device 1. The feedback mechanism 10 is arranged to notify a user of a start of expulsion of medicament from the medicament container 25.

According to the present example, the plunger rod 11 has a radial opening 11a, and the tubular extension member 5 which is arranged to receive the plunger rod 11 has a corresponding flexible tongue 5a flexible in the radial direction and arranged to engage with the opening 11a. The tubular rotator 17 is arranged to receive a portion of the tubular extension member 5, in particular that portion which comprises the flexible tongue 5a.

The tubular rotator 17 is rotatable from an initial rotational position to a final rotational position. In its initial rotational position the tubular rotator 17 is arranged to push the flexible tongue 5a into engagement with the opening 11a, preventing the plunger rod 11 from axial displacement. When the tubular rotator 17 is rotated, the inner structure of the tubular rotator 17 is designed such that it will provide less radial force on the flexible tongue 5a, allowing the flexible tongue 5a to flex radially outwards to disengage from the plunger rod 11. The plunger rod 11, which is biased in the proximal direction, is thereby displaced axially and medicament administration is thus commenced as the plunger rod 15 pushes the plunger 13 inside the medicament container 25.

Figure 3A:
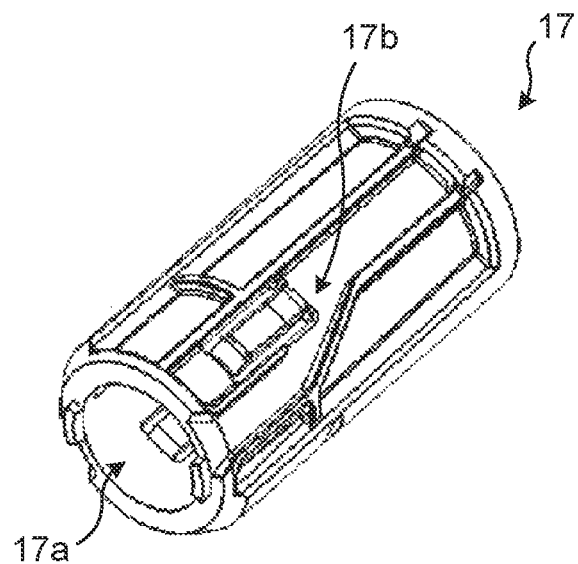
FIG. 3a is a perspective view of one example of a rotator.
Figure 3B:
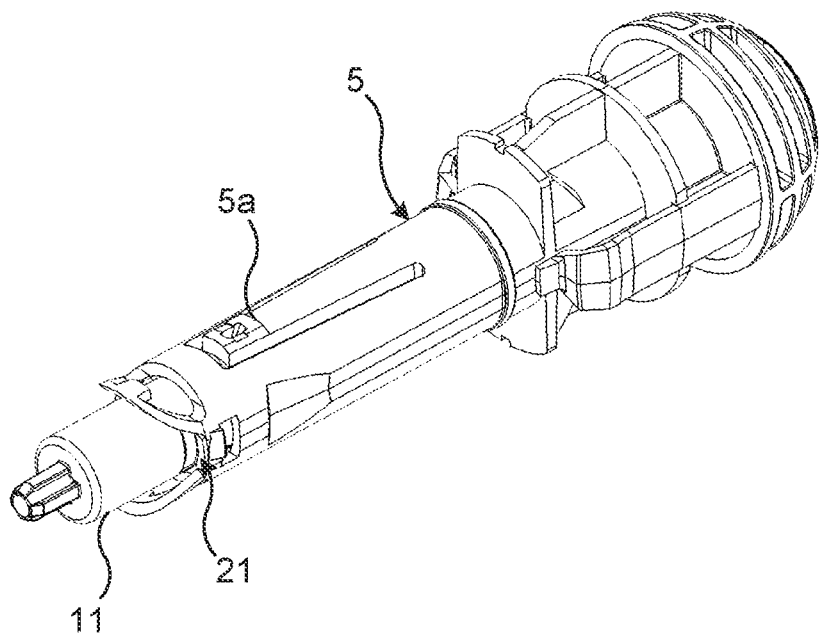
FIG. 3b is a perspective view of one example of a tubular extension member and plunger rod.

As shown in FIG. 3a, the tubular rotator 17 has a central through-opening 17a extending from the proximal end to the distal end of the tubular rotator 17. The tubular rotator 17 is arranged to receive the tubular extension member 5 and the plunger rod 11 in the through-opening 17a.

The tubular rotator 17 furthermore comprises a guide structure 17b. The guide structure 17b is arranged to interact with the medicament delivery member cover 7, in particular to convert linear motion of the medicament delivery member cover 7 to rotational motion of the tubular rotator 17.

Figure 4A:
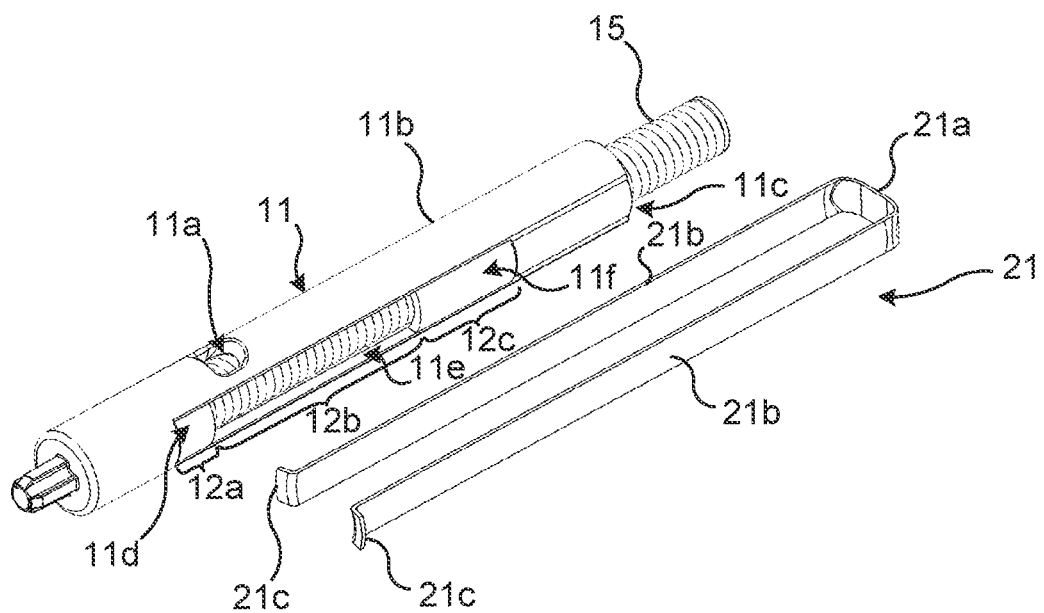
FIGS. 4a and 4b are perspective views of an example of a plunger rod and a U-bracket.

FIG. 4a shows a first example of a plunger rod 11, and U-bracket 21. The U-bracket 21 has a distal transversal end portion 21a and two legs 21b connected by the distal transversal end portion 21a. Moreover, the U-bracket 21 has two radial feet 21c. Each radial foot 21c extends from a respective leg 21b.

The plunger rod 11 has a hollow body 11b and a distal end opening 11c. The plunger rod 11 is arranged to receive the first energy accumulation member 15 in the distal end opening 11c, such that the first energy accumulation member 15 extends in the distal direction out from the distal end opening 11d. The plunger rod 11 is arranged to retain the proximal end of the first energy accumulation member 15 in the hollow body 11b to enable biasing by means of the first energy accumulation member 15. The U-bracket 21 is arranged to receive the plunger rod 11, from the distal end of the plunger rod 11, and the first energy accumulation member 15 is arranged to be compressed between the distal transverse end portion 21a and a stop inside the plunger rod 11 when the plunger rod 11 is in the initial position. In the initial position of the plunger rod 11, the radial feet 21c are in engagement with the rear end cap 5.

The exemplified plunger rod 11 has an external surface that has a first section 12a provided with a first guide structure 11d arranged to support the U-bracket 21 and flex the U-bracket 21 radially outwards to enable the radial feet 21c to engage with the tubular extension member 5. The first section 12a, and in particular the first guide structure 11d, has a dimension in the transverse direction perpendicular to the longitudinal direction of the plunger rod 11, which is greater than the distance between the two radial feet 21c in a radially unbiased state of the U-bracket 21. The first guide structure 11d hence pushes the U-bracket 21 radially outwards when the U-bracket bears against the first guide structure 11d. The first guide structure 11d includes axial grooves, of which only one is shown in FIG. 4a; the other one being at 180 degrees relative to the illustrated axial groove. The first guide structure 11d facilitates guiding relative linear movement between the plunger rod 11 and the U-bracket. In particular, the legs 21b are arranged to slide in the axial grooves 11d.

In the initial position of the plunger rod 11 the axial overlap of the first section 12a, in particular the first guide structure 11d, and the U-bracket 21 corresponds to the distance of axial displacement of the plunger rod 11 necessary for commencement of medicament expulsion. This distance corresponds to the distance from the proximal end of the plunger rod 11 to the distal end of the plunger 13, in the initial position of the plunger rod 11. The initial overlap may be a little longer or a little shorter than the distance from the proximal end of the plunger rod to the distal end of the plunger. This applies to any variation disclosed herein.

The plunger rod 11 has a second section 12b arranged distally from and contiguous to the first section 12a. According to the present example, the second section 12b is defined by a longitudinal axially extending radial opening 11e allowing radial inwards flexing of the U-bracket 21 towards its radially unbiased state. To this end, in the second section 12b the channel forming the distal end opening 11c is open to the sides, i.e. in the radial direction. The longitudinal axially extending radial opening 11e has a longitudinal extension aligned with the first guide structure 11d. The transverse dimension of the plunger rod 11 is here due to the longitudinal axially extending radial opening 11d smaller than it is in the first section 12a. The U-bracket 21 is allowed to flex radially inwards towards its radially unbiased state, only limited by the diameter of the first energy accumulation member 15. This radial inwards flexing of the U-bracket 21 is sufficient to disengage the radial feet 21c from the rear end cap 5.

The exemplified plunger rod 11 furthermore has a third section 12c arranged distally from and contiguous to the second section 12b. The third section 12c is defined by a second guide structure 11f arranged to guide the U-bracket 21 axially. The second guide structure 11f is axially aligned with the longitudinal extending radial opening 11e. The second guide structure 11f may for example comprise two axial grooves, of which one is shown in FIG. 4a. The second guide structure 11f has a greater transverse dimension than the longitudinal axially extending radial opening 11d. To this end, the third section 12c is arranged to support and flex the U-bracket 21 radially outwards allowing the U-bracket to again engage with the tubular extension member 5.

Figure 4B:
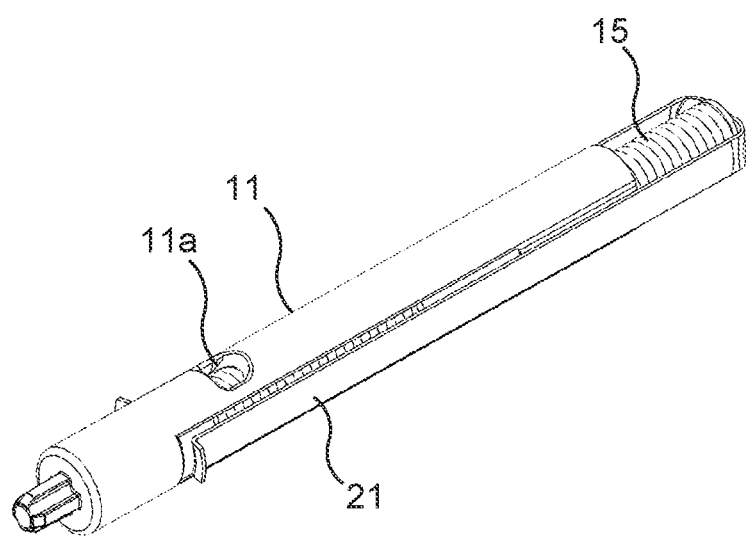

FIG. 4b shows the plunger rod 11 and the U-bracket 21 in a mounted state, i.e. when the U-bracket 21 has received the plunger rod 11. This is in particular their relative position in the initial position of the plunge rod 11. It may be seen that the first energy accumulation member 15 is in a compressed state in which it biases the plunger rod 11 in the proximal direction and the U-bracket 21 in the distal direction. It should here be noted that this compressed state is obtained when the plunger rod 11 is prevented from axial displacement by engagement with the flexible tongue 5a of the tubular extension member 5 and the U-bracket 21 is in engagement with the tubular extension member 5.

Figure 5A:
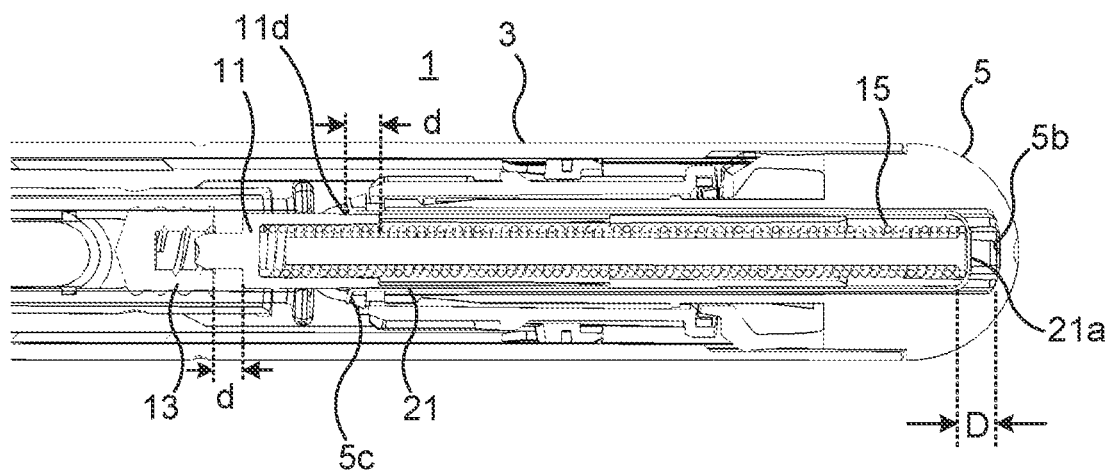
FIGS. 5a, 5b, and 5c show longitudinal sections of a portion of the medicament delivery device in FIG. 2 in a state prior to use, during use, and after use, respectively.
Figure 5B:
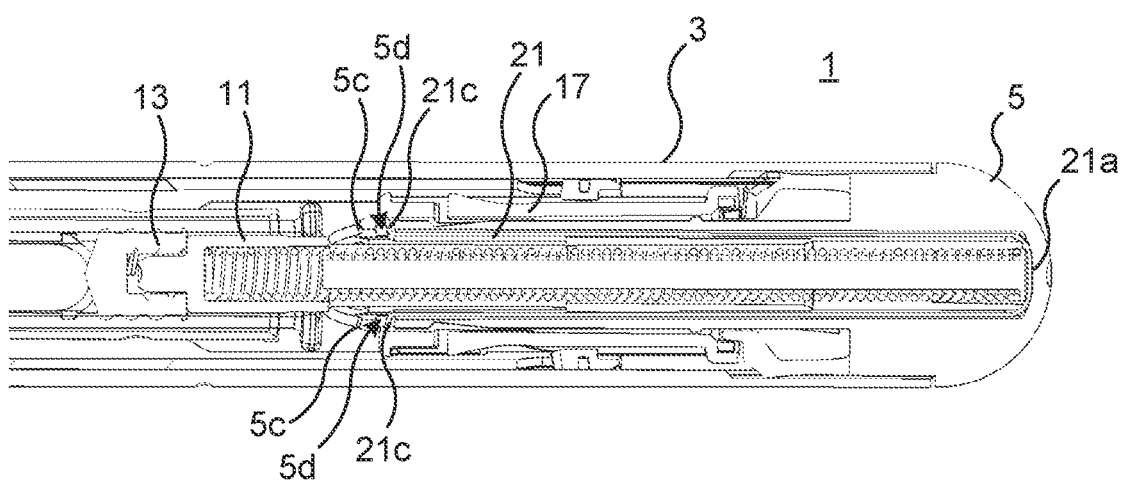
Figure 5C:
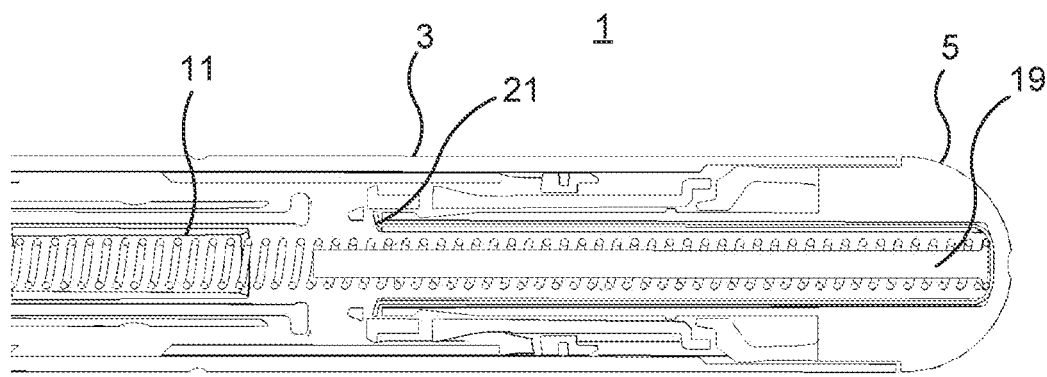

With reference to FIGS. 5a-c the operation of the plunger rod 11 and the U-bracket 21 will now be described in more detail. In FIG. 5a the medicament delivery device 1 is in a state ready for use. The plunger rod 11 is in the initial position. The U-bracket 21 is in a first position in which it bears against the first section 12a, in particular the first guide structure 11d. The U-bracket 21 is hence flexed radially and in engagement with the tubular extension member 5. The tubular extension member 5 has first engagement means 5c for engagement with the U-bracket 21. The first engagement means 5c may for example be a proximal end edge of the tubular extension member 5 or radial recess, with which the radial feet 21c may engage. The first energy accumulation member 15 is hence in a compressed state, biasing the plunger rod 11 and the U-bracket 21 in opposite directions. The tubular extension member 5 has a distal inner surface 5b defining a distal end of the central opening of the tubular extension member 5 in which the plunger rod 11 and the U-bracket 21 are arranged. The U-bracket 21 is distanced by distance D from the distal inner surface 5b.

The plunger rod 11 and the plunger 13 are in contact with each other in the initial position of the plunger rod 11. There is however a play, or distance d, between the plunger rod 11 and the distal end of the plunger 13. The plunger rod 11 has to be displaced the distance d before it can displace the plunger 13 axially. This distance d corresponds to the distance that the plunger rod 11 must travel in order for medicament expulsion to commence. This is also the size of the axial overlap of the first section 12a and the U-bracket 21 in the initial position of the plunger rod 11.

In FIG. 5b, the medicament delivery device 1 is shown during medicament expulsion. Here, the plunger rod 11 has been released from engagement with the tubular extension member 5 due to the rotation of the tubular rotator 17. In the illustration in FIG. 5b, the plunger rod 11 has been displaced in the proximal direction and it has bridged the initial gap, or distance d, to the plunger 13. Medicament expulsion has hence commenced. The U-bracket 21 has moreover been released from its initial engagement with the rear end cap 5, as the displacement of the plunger rod 11 has resulted in that the second section 12b of the plunger rod 11 has reached the proximal end of the U-bracket 21, whereby the U-bracket 21 has been able to flex radially inwards towards its radially unbiased position. The U-bracket 21 has thus been rapidly displaced in the distal direction until reaching the distal inner surface 5b of the tubular extension member 5. The opposite directional motion of the plunger rod 11 and the U-bracket 21 is generally shown by the two arrows. This collision results in an audible "click", and in vibration of the medicament delivery device 1. The user hence becomes aware of that medicament expulsion has commenced. The user may then, for example, count 10-15 seconds before removing the medicament delivery device 1 from the injection site.

The U-bracket 21 may in its end position in which it has collided with the distal inner surface 5b, engage with the tubular extension member 5. The tubular extension member 5 may therefore have radial openings 5d arranged distally from and aligned with the first engagement means 5c. In particular, the radial feet 21c may be received in the radial openings 5d to enable the plunger rod 11 to move past the U-bracket 21 during medicament expulsion, in particular as the third section 12c passes by the proximal end of the U-bracket 21. FIG. 5c shows the medicament delivery device 1 in a final state, after medicament delivery has been finalised and the plunger rod 11 has moved past the U-bracket 21 in the proximal direction.

Figure 6:
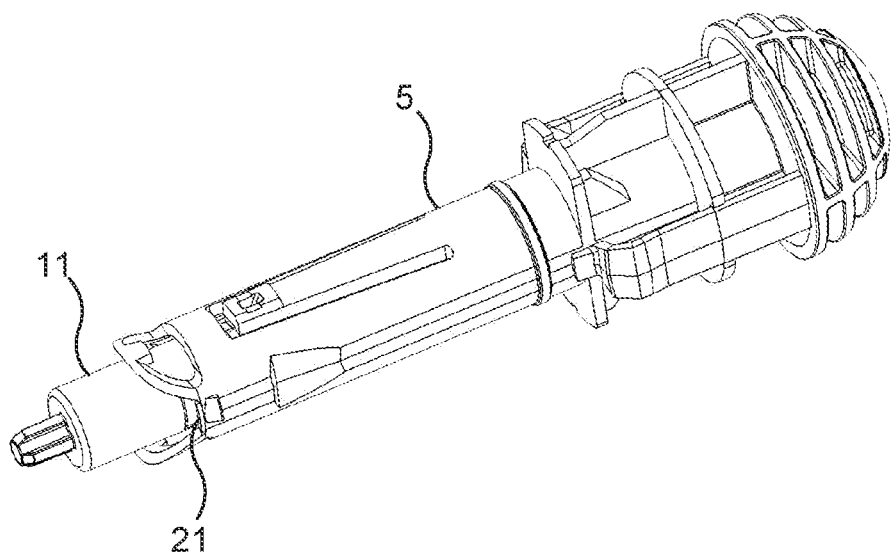
FIG. 6 is a perspective view of another example of a tubular extension member and plunger rod.
Figure 7A:
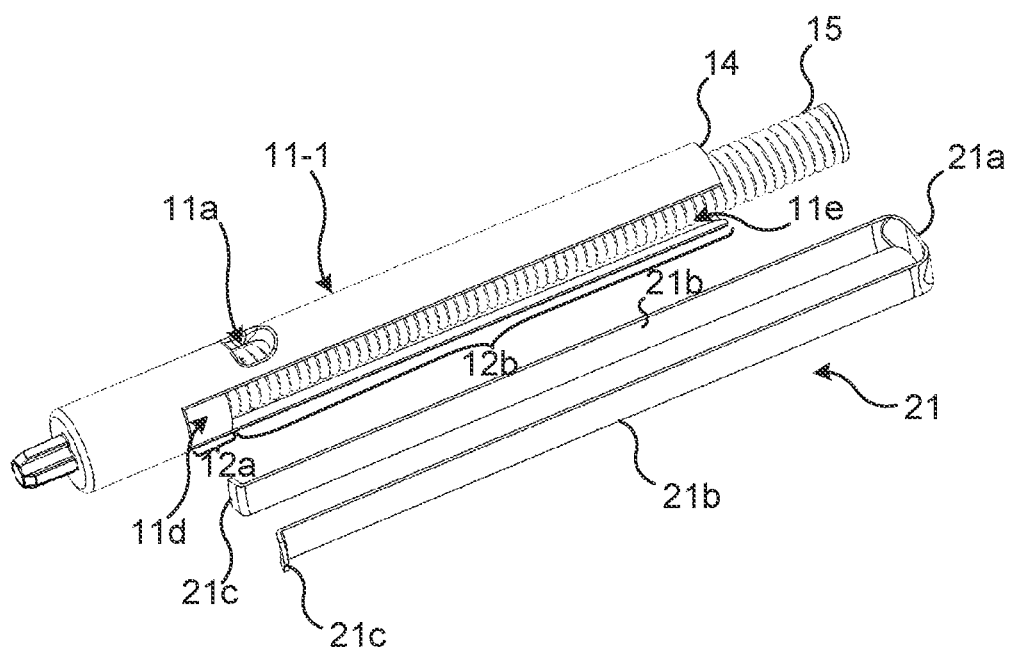
FIGS. 7a and 7b are perspective views of the plunger rod and a U-bracket of the example in FIG. 6.

FIG. 6 shows a second example of a tubular extension member 5 and a plunger rod 11-1. FIG. 7a shows the plunger rod 11-1 in more detail. Plunger rod 11-1 is similar to the previously described plunger rod 11. Plunger rod 11-1 also has a first section 12a like plunger rod 11, i.e. with a first guide structure 11d. Plunger rod 11-1 however has a second section 12b arranged distally from and contiguous to the first section 12a, which second section extends to the distal end 14 of the plunger rod 11-1. The second section 12b is also in this example defined by a longitudinal axially extending radial opening 11e allowing radial inwards flexing of the U-bracket 21 towards its radially unbiased state. To this end, in the second section 12b may be formed by two axial cut-outs extending from the distal end 14 of the plunger rod 11-1 to first section 12a, splitting the distal portion of the plunger rod 11-1. The longitudinal axially extending radial opening 11e has a longitudinal extension aligned with the first guide structure 11d. The transverse dimension of the plunger rod 11 is due to the longitudinal axially extending radial opening 11d smaller than it is in the first section 12a. The U-bracket 21 is here allowed to flex radially inwards towards its radially unbiased state, only limited by the diameter of the first energy accumulation member 15. This radial inwards flexing of the U-bracket 21 is sufficient to disengage the radial feet 21c from the rear end cap 5.

Figure 7B:
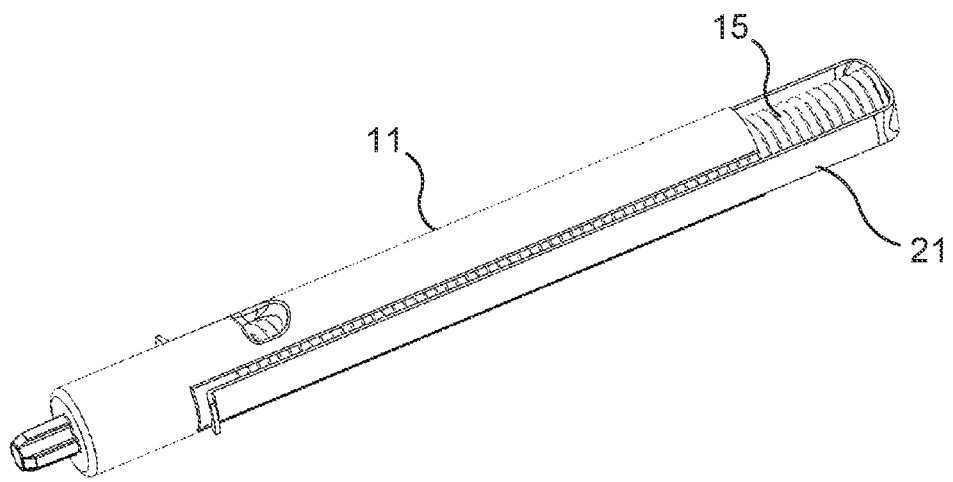

The operation of this variation of the medicament delivery device 1 is similar to that described above with reference to FIGS. 5a-c. The tubular extension member 5 does however not have radial openings arranged distally from the first engagement means in order to enable the plunger rod 11-1 to pass the U-bracket 21. Since the open second section 12b of plunger rod 11-1 extends until the distal end 14, the U-bracket 21 can be accommodated in the longitudinal axially extending radial opening the entire way as the plunger rod 11-1 moves past the U-bracket 21. FIG. 7b shows the plunger rod 11-1 and the U-bracket 21 in an assembled state.

Figure 8:
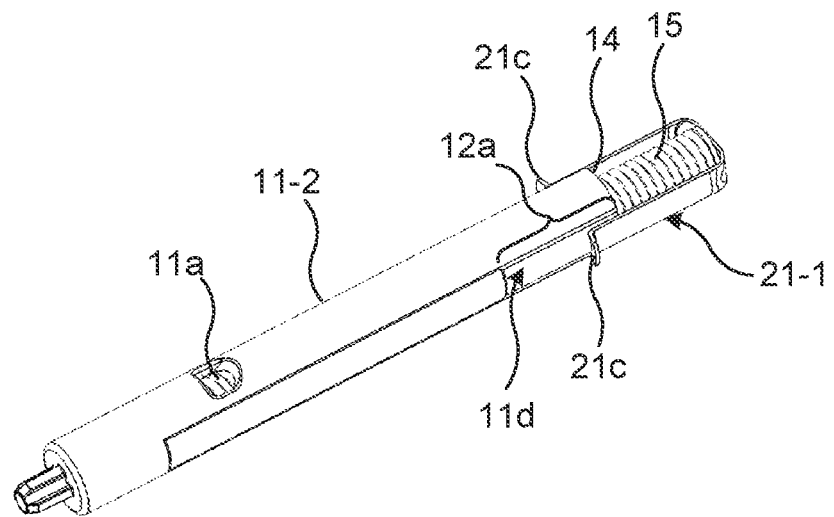
FIG. 8 is a perspective view of yet another example of a plunger rod and a U-bracket.

With reference to FIG. 8 another example of a plunger rod and U-bracket is shown. According to this variation, the U-bracket 21-1 is shorter relative to the plunger rod 11-2 than the U-bracket 21 is relative to the plunger rods 11 and 11-1. Plunger rod 11-2 is adapted to the design of U-bracket 21-1. To this end, plunger rod 11-2 has an external surface that has a first section 12a provided with a first guide structure 11d arranged to support the U-bracket 21-1 and flex the U-bracket 21-1 radially outwards to enable the radial feet 21c to engage with the tubular extension member 5. The first section 12a, and in particular the first guide structure 11d, has a dimension in the transverse direction perpendicular to the longitudinal direction of the plunger rod 11-2, is greater than the distance between the radial feet 21c in the radially unbiased state of the U-bracket 21-1. The first guide structure 11d hence pushes the U-bracket 21-1 radially outwards when the U-bracket bears against the first section 12a.

The first guide structure 11d includes axial grooves, of which only one is shown in FIG. 8. The first guide structure 11d facilitates guiding relative linear movement between the plunger rod 11-2 and the U-bracket 21-1.

The first section 12a extends the entire way to the distal end 14 of the plunger rod 11-2. In the initial position of the plunger rod 11-2 the axial overlap between the first section 12a and the U-bracket 21-1 corresponds to the distance of axial displacement of the plunger rod 11-2 necessary for commencement of medicament expulsion.

Figure 9A:
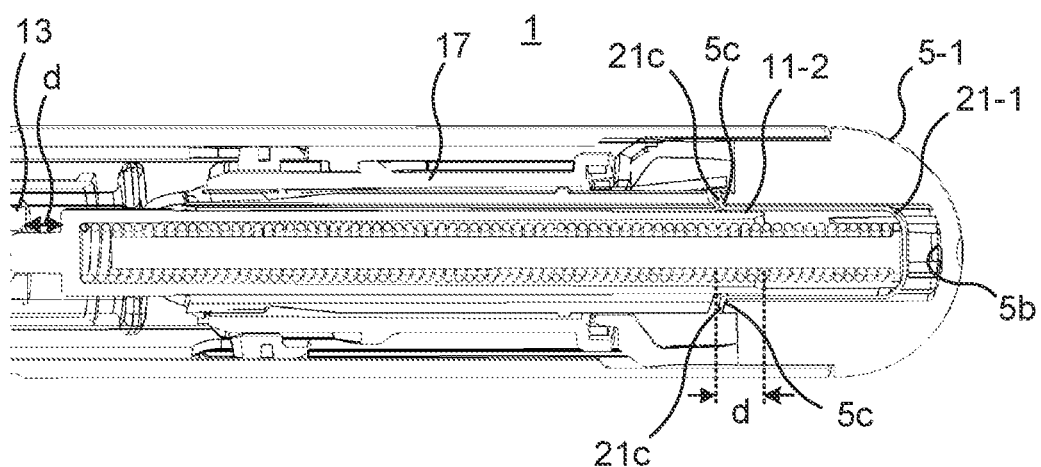
FIGS. 9a and 9b show longitudinal section of a portion of a medicament delivery device comprising the plunger rod and U-bracket in FIG. 8 in a state prior to use and during use, respectively.
Figure 9B:
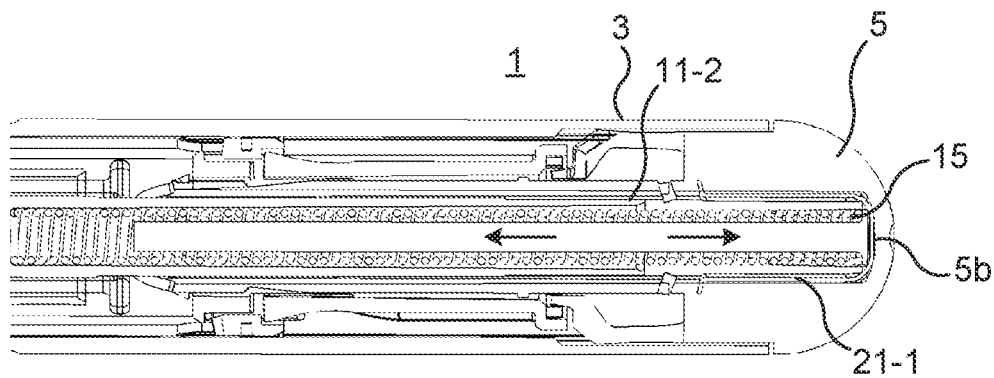

FIGS. 9a-9b show the operation of a medicament delivery device 1 including the plunger rod 11-2 and the U-bracket 21-1. The tubular extension member 5-1 has first engagement means 5c, which in the present case are exemplified by radial openings. As shown in FIG. 9a the radial feet 21c of the U-bracket 21-1 are initially, i.e. in the initial position of the plunger rod 11-2, in engagement with the radial openings. When the plunger rod 11-2 is released by rotation of the tubular rotator 17, the plunger rod 11-2 is displaced in the proximal direction bridging the gap d between the distal end of the plunger 13 and the proximal end of the plunger rod 11-2. The plunger rod 11-2 will thus generally have been displaced enough to slide out beneath the U-bracket 21-1 to thereby allow the U-bracket 21 to flex radially inwards towards its radially unbiased state. The U-bracket 21 is hence disengaged from the tubular extension member 5-1 and is thereby due to its biased state rapidly displaced in the distal direction, subsequently colliding with the distal inner surface 5b of the tubular extension member 5-1. Again, audible "click" is thereby generated, and vibrations are induced in the medicament delivery device 1. FIG. 9b shows when the U-bracket 21 has collided with the distal inner surface 5b.

Any variation disclosed herein may be utilised with an electromechanical sensor and a recording unit provided with electronic components, and which recording unit may be attachable to and detachable from the housing. The electromechanical sensor may be arranged to detect when the U-bracket collides with the distal inner surface. According to this variation the medicament delivery device includes an injection end member which is axially displaceable and arranged to interact with the U-bracket. The tubular extension member has a distal through-opening in which the injection end member is movably arranged. When medicament expulsion commences, the U-bracket is released and due to the biasing provided by the first energy accumulation member, is pushed in the distal direction. As a result the injection end member which is axially aligned and located distally relative to the U-bracket, is pushed axially in the distal direction by the U-bracket, as allowed by its free location in the distal through-opening. The injection end member will thereby actuate the electromechanical sensor arranged to detect displacement of the injection end member when medicament expulsion is commenced. In this manner detection of commencement of medicament expulsion may be presented to the user by the recording unit or by an external device in communication with the recording unit.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A medicament delivery device that notifies a user of a start of expulsion of medicament from a medicament container, wherein the medicament delivery device comprises:
   a housing;
   a needle cover slidably positioned within the housing and having a first axial position and a second axial position;
   a signal generating member comprising two proximally extending legs;
   a plunger rod releasably fixed relative to the housing in a pre-tensioned state, where the plunger rod is hollow and has an open distal end and a proximal end; and
   a spring positioned within the plunger rod, where the spring is compressed when the plunger rod is in the pre-tensioned state biasing the proximal end to move the plunger rod proximally and biasing the signal generating member to axially move in a distal direction,
   wherein the signal generating member is arranged to partially surround the plunger rod,
   wherein axial movement of the needle cover from the first axial position to the second axial position releases the plunger rod causing decompression of the spring so that the spring simultaneously drives the signal generating member distally relative to the housing to generate an audible signal indicating that medicament expulsion from the medicament container has just commenced.

2. The medicament delivery device of claim 1, wherein the signal generating member is U-Shaped and has a distal transversal end portion.

3. The medicament delivery device of claim 1, wherein each leg comprises a foot at a terminal proximal end.

4. The medicament delivery device of claim 1, wherein the legs flex radially prior to the generation of the audible signal.

5. The medicament delivery device of claim 1 further comprises a rod that is positioned within the spring, where the rod has a longitudinal axis.

6. The medicament delivery device of claim 5, wherein the signal generating member flexes radially relative to the longitudinal axis when the needle cover moves from the first axial position to the second axial position.

7. The medicament delivery device as claimed in claim 1 wherein the signal generating member comprises an elongated U-shaped bracket supporting the two proximally extending legs, where each leg is flexible and is provided with radial feet extending radially relative to a longitudinal axis of the housing.

8. The medicament delivery device as claimed in claim 1, wherein the plunger rod has an external surface configured to operatively engage the legs of the signal generating member radially outwards, and to guide axial displacement of the signal generating member.

\* \* \* \* \*